(12) United States Patent
Hirosawa et al.

(10) Patent No.: US 6,486,951 B2
(45) Date of Patent: Nov. 26, 2002

(54) METHOD OF EVALUATING AN ANISOTROPIC THIN FILM AND AN EVALUATING APPARATUS

(75) Inventors: Ichiro Hirosawa, Tokyo (JP); Daisuke Tanooka, Aichi (JP)

(73) Assignees: NEC Corporation, Tokyo (JP); Nippon Laser & Electronics Lab., Aichi (JP)

( * ) Notice: Subject to any disclaimer, the term of this patent is extended or adjusted under 35 U.S.C. 154(b) by 56 days.

(21) Appl. No.: 09/816,300

(22) Filed: Mar. 23, 2001

(65) Prior Publication Data

US 2001/0024277 A1 Sep. 27, 2001

(30) Foreign Application Priority Data

Mar. 24, 2000 (JP) ........................................ 2000-084167

(51) Int. Cl.$^7$ .................................................. G01J 4/00
(52) U.S. Cl. ..................................................... 356/369
(58) Field of Search ................................ 356/364, 369, 356/630, 631; 250/225

(56) References Cited

U.S. PATENT DOCUMENTS

| 5,185,644 A | * | 2/1993 | Shimoyama et al. | .... 101/351.1 |
| 5,757,671 A | * | 5/1998 | Drevillon et al. | ........... 250/225 |
| 5,929,994 A | * | 7/1999 | Lee et al. | ................... 250/228 |
| 6,052,188 A | * | 4/2000 | Fluckiger et al. | ........... 356/369 |
| 6,073,464 A | * | 6/2000 | Boher et al. | ............. 219/121.6 |
| 6,304,326 B1 | * | 10/2001 | Aspnes et al. | ........... 356/243.1 |
| 6,307,627 B1 | * | 10/2001 | Vurens | ........................ 250/225 |
| 6,356,347 B1 | * | 3/2002 | Watanabe et al. | ........... 250/225 |

FOREIGN PATENT DOCUMENTS

| JP | 03-065637 | 3/1991 | .......... G01N/21/41 |
| JP | 04-095845 | 3/1992 | .......... G01M/11/00 |
| JP | 05-005699 | 1/1993 | .......... G01N/21/23 |
| JP | 07-151640 | 6/1995 | .......... G01M/11/00 |
| JP | 09-218133 | 8/1997 | .......... G01M/11/00 |
| JP | 2000-121496 | 4/2000 | .......... G01M/11/00 |
| WO | WO-92/12404 A1 | * 7/1992 | ................. 356/364 |

* cited by examiner

*Primary Examiner*—Ricky Mack
(74) *Attorney, Agent, or Firm*—Hayes Soloway P.C.

(57) ABSTRACT

In an apparatus for evaluating an anisotropic thin film, an optical system generates a light beam having a predetermined diameter and polaraization state to project the light beam as incident light into a thin film sample corresponding to the anisotropic thin film. An analyzer is disposed at an optically down stream side of the thin film sample. At an optically down stream side of the analyzer, a two-dimensional photo-intensity detector is disposed to detect reflected light, obtained from the thin film sample, through the analyzer. The detector produces a light intensity distribution. On the basis of the light intensity distribution, an evaluating unit evaluates an inplane distribution of an optical anisotropy of the thin film sample.

20 Claims, 9 Drawing Sheets

METHOD OF EVALUATING AN ANISOTROPIC THIN FILM AND AN EVALUATING APPARATUS

BACKGROUND OF THE INVENTION

This invention relates to a method of evaluating a thin film having optical anisotropy, such as a crystal oriented film for providing crystal particles with an initial orientation.

As a method of evaluating the anisotropic thin film, there is known a method using a reflected light, which is disclosed in such as Japanese Unexamined Patent Publications (JP-A) Nos. 3-65637 (first prior art), 9-218133 (second prior art), 7-151640 (third prior art), and 5-5699 (fourth prior art).

The first prior art discloses a method of measuring anisotropy on the basis of an incident angle and dependency of an incident direction of the reflected light intensity. The second prior art discloses a method of determining dielectric constant, film thickness, and a direction of a main dielectric constant coordinate of an oriented area, and dielectric constant and film thickness of unoriented area. The third prior art discloses a method of measuring the anisotropy in accordance with two color differences by using of a infrared radiation. The fourth prior art discloses a method of measuring the anisotropy by changing the incident angle by using of a visible ray.

As the anisotropic thin film, there is known a crystal oriented film which is subjected to an orientation treatment for use in a liquid crystal display component. A method of evaluating such a film is disclosed in Japanese Unexamined Patent Publication (JP-A) 4-95845 (fifth prior art). Particularly, the fifth prior art discloses a method of evaluating the anisotropy by measuring reflected light intensity which is generated when a linear polarization is projected in the film.

In an inorganic material having high-level crystalline, a relation between crystal structure and optical anisotropy of a thin film has been clarified. Therefore, it is possible by the methods of the first through the third prior arts to quantitatively evaluate the crystal orientation equal to a particle orientation. However, there is a problem in each of the methods that dimensions to be measured at a one time becomes narrow or it takes more time for measuring.

On the other hand, there is known a method for evaluating the anisotropy of a film by projecting a P polarized light into a thin film sample at an angle of polarization of a substrate, and measuring an intensity of S polarization component of a reflected light (see JP-A 2000-121496). With this method, it becomes possible to make the intensity of P polarization component in the reflected light minimum by projecting the P polarized light at an angle of polarization. So that, there is increased accuracy of measuring the intensity of the light having S polarization component which is generated by the anisotropy of the film. In a case where the anisotropic film is directly formed on the substrate, it is possible to make the P polarization component in the reflected light minimum by projecting the P polarized light at an angle of polarization on the substrate. Generally, however, when a sample having a multifilm structure such as the liquid crystal display component is used, it can not be possible to define with accuracy the angle of polarization which lacks of P polarization component of the reflected light so that it becomes difficult to apply this method.

Furthermore, S polarization component is included in the reflected light generated in response to the incidence of the P polarization. The S polarization component has an amount which depends on a degree of the optical anisotropy and a thickness of the area having the optical anisotropy of the sample. Particularly, the amount becomes small as the anisotropy is smaller or the thickness becomes thinner. As a result, limitation of detecting the optical anisotropy is determined by the intensity of the light source and sensitivity of a detector. Therefore, it is difficult to improve the detecting sensitivity.

The fourth prior art discloses a method of evaluating liquid crystal orientation of the oriented film by using an amount of the reflected light on a surface of the oriented film when the linear polarization is projected on the surface of the oriented film. However, the intensity of the reflected light generated in response to the incidence of the linear polarization having an arbitrary vibrating direction depends on not only the refractive index of the film but the thickness of the film. Therefore, in the fourth prior art, it is difficult to detect the anisotropy of the refractive index from the intensity of the reflected light.

Additionally, as disclosed in the fifth prior art, when the linear polarization is projected on the surface of the sample in perpendicular, the incident light and the reflected light pass through the same optical path. However, it is impossible to arrange the light source and the photo-intensity detector on the same optical path, and it is also impossible to carry out the perpendicular incidence.

When a beam splitter is used, it is unnecessary to arrange the light source and the photo-intensity detector on the same optical path. However, this beam splitter is not for maintaining the polarized state of the reflected light and a transparent light, so that it becomes impossible to carry out the perpendicular incidence.

In the fifth prior art, the light is projected into the surface of the film not in perpendicular but at an inclined angle. In this case, the incident light and the reflected light have two components. One of the components is S polarization component as a vibration component parallel to the sample surface. Another of the components is P polarization component as a vibration component perpendicular to both of the through direction of the light and the S polarization component. When the sample has same optical direction, the P polarization component and the S polarization component have different refractive indexes each other. When the light is projected into the sample surface at a predetermined angle, the polarized state of the incident light is specified as S polarization.

It is to be noted the P polarization component does not have the vibration direction parallel to or perpendicular to the film surface. In order to project the light of vibration direction parallel to a rubbing direction, namely, the direction of the orientation treatment, it is necessary to project the S polarized light into the sample in a direction perpendicular to the rubbing direction. On the other hand, in order to project the light of the vibration direction perpendicular to the rubbing direction, it is necessary to project the S polarized light in the direction in parallel with the rubbing direction.

In particular, in the case of using the liquid crystal oriented film which is subjected with the orientation treatment by rubbing the film surface with a cloth, a grooved anisotropic irregularity is produced on the film surface almost in parallel with the rubbing direction. Since the intensity of the reflected light becomes different according to the incident direction because of its anisotropic surface state, it is impossible to measure in accurate the optical anisotropy of the film by the method disclosed in the fifth prior art.

Furthermore, when a sample of which orientation direction is unknown is used, the light is not projected so that S polarization direction becomes parallel to or perpendicular to the orientation direction.

As mentioned above, according to the fifth prior art, it is impossible to measure in accurate the anisotropy of the film on the basis of the result of measuring the intensity of the reflected light generated when the linear polarization is projected in the sample surface.

SUMMARY OF THE INVENTION

It is therefore an object of the present invention to provide a method of evaluating an anisotropic thin film, which is capable of evaluating an inplane distribution of an optical anisotropy of the thin film material in high speed and accurate.

It is another object of the present invention to provide an evaluating apparatus, which is capable of evaluating the inplane distribution of the optical anisotropy of the think film material in high speed and accurate.

Other objects of the present invention will become clear as the description proceeds.

According to the present invention, there is provided a method for evaluating an anisotropic thin film. The method comprises the steps of using a lens, a polarizer, and a phase converter to generate a light beam having a predetermined diameter and polarization state and to project the light beam as incident light into a thin film sample corresponding to the anisotropic thin film, detecting, by a two-dimensional photo-intensity detector through an analyzer, reflected light obtained from the thin film sample to produce a light intensity distribution, and evaluating an inplane distribution of an optical anisotropy of the thin film sample on the basis of the light intensity distribution.

According to the present invention, there is provided an evaluating apparatus for evaluating an anisotropic thin film. The evaluating apparatus comprising an optical system comprising lens, a polarizer, and a phase converter, the optical system generating a light beam having a predetermined diameter and polaraization state to project the light beam as incident light into a thin film sample corresponding to the anisotropic thin film, an analyzer disposed at an optically down stream side of the thin film sample, a two-dimensional photo-intensity detector disposed at an optically down stream side of the analyzer for detecting reflected light, obtained from the thin film sample, through the analyzer to produce a light intensity distribution, and an evaluating unit connected to the two-dimensional photo-intensity detector for evaluating an inplane distribution of an optical anisotropy of the thin film sample on the basis of the light intensity distribution.

When Rpp (p polarization component of the reflected light generated by projecting the P polarization), Rsp (s polarization component of the reflected light generated by projecting the P polarization), Rps (p polarization component of the reflected light generated by projecting the S polarization) and Rss (S polarization component of the reflected light generated by projecting the S polarization) are given for complex vibration index regarding the p component and S component of the reflected light which is generated by projecting p polarization or S polarization into the anisotropic thin film, Rsp and Rps have values if the sample in optically anisotropic, and have zero if the sample is optically isotropic.

Generally, absolute values of Rsp and Rps are very small for absolute values of Rpp and Rss. As the optical anisotropy of the sample becomes small, the absolute values of Rsp and Rps become small. In the method of measuring the anisotropy by combining only a polarizer and a detector, detected intensity is in proportion to squire of the absolute value of Rsp. Therefore, the detected intensity is quickly weakened when the optical anisotropy of the film becomes small.

On the other hand, in the optical system by combining the polarizer, a phase converter, and the analyzer of the present invention, it is possible to make the intensity of the light zero, which permeates the lowest detector against arbitrary combination of Rss, Rps, Rsp and Rpp. Namely, it is possible to change the reflected light from the film of the arbitrary optical character to the linear polarization in an upper stream. This kind of the linear polarization is generally given as:

$$a \times Rss + b \times Rps + c \times Rsp + d \times Rpp \quad (1)$$

where a, b, c, and d are arbitrary complex numbers.

When the sample is isotropic, the linear polarization is given as:

$$a \times Rss + d \times Rpp. \quad (2)$$

When the direction of the analyzer is arranged so as to be an extinction state for the light of (a×Rss+d×Rss), the detected intensity of the light from the anisotropic sample which is given by (a×Rss+b×Rps+c×Rsp+d×Rss) is leaded as:

$$(a^* \times Rss^* + d^* \times Rpp^*) \times (b \times Rps + c \times Rsp) + (a \times Rss + d \times Rpp) \times (b^* \times Rps^* + c^* \times Rsp^*) \quad (3)$$

where a*, Rss*, D*, Rpp*, b*, Rps*, c*, Rsp* are conjugation complexes of a, Rss, d, Rpp, b, Rps, c, Rsp, respectively. As shown in Equation (3), primary term is included for the small amount of Rsp and Rps, and the conjugation complex thereof. The arrangement comprising the polarizer, the phase converter and the analyzer includes the terms proportional to small amount of primary Rsp and Rps of which the detected intensity has high-level relation with the anisotropy of the sample. Therefore, this method is higher in sensitivity for the anisotropy than the method of evaluating the anisotropy by combining the polarizer and the analyzer of the detected intensity of the small amount of secondary Rsp and Rps.

As mentioned above, in the present invention, the intensity detected by the arrangement of the combination with the polarizer, the phase converter and the analyzer includes the component proportional to the complex vibration refractive index of the p polarization and the s polarization component which are generated by projecting p polarization caused by the anisotropy of the film and s polarization p polarization, respectively. Therefore, the polarized state of the reflected light which is generated by projecting the light of the constant polarized state into the thin film sample of the optical anisotropy is changed in accordance with the incident direction of the light to the sample because of the optical anisotropy of the film. It is possible to select an appropriate incident direction in order to measure the inplane distribution of the optical anisotropy of the film by using the sample state having inplane rotating mechanism. Furthermore, it becomes possible to measure the inplane distribution of the optical anisotropy at an wide area by using the stage having the parallel moving mechanism.

DESCRIPTION OF THE PREFERRED EMBODIMENT

Description will be made about various evaluating apparatus according to embodiments of the present invention. Each of the evaluating apparatus is for evaluating an anisotropic thin film.

Figure 1:
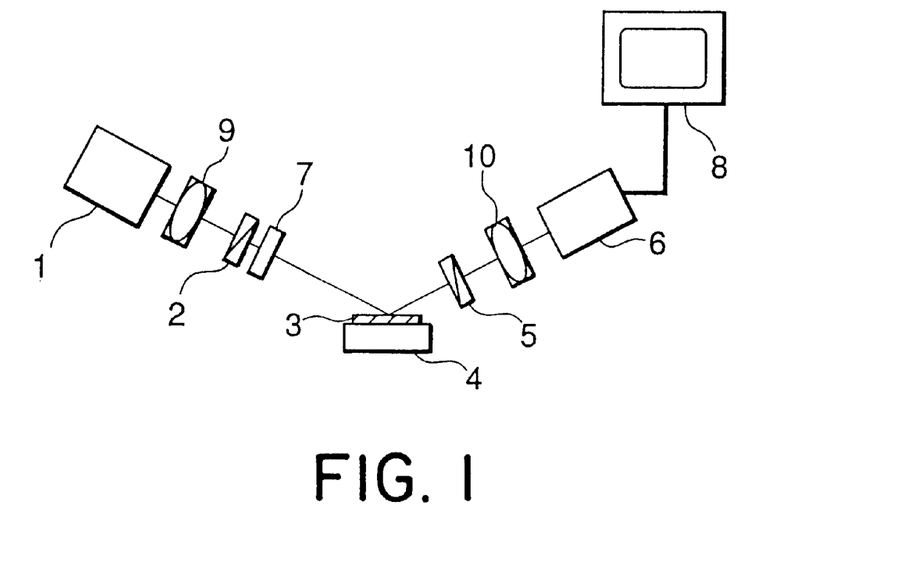
FIG. 1 is a schematic diagram of an evaluating apparatus according to a first embodiment of the present invention.

Referring to FIG. 1, an evaluating apparatus according to a first embodiment of the present invention comprises a single light source 1, a polarizer 2, a sample state 4, an analyzer 5, CCD camera 6 used as a two-dimensional photo-intensity detector, a quarter wavelength board 7 used as a phase converter, a monitor 8, beam expander 9, and a condenser lenses 10. A He—Ne laser is used as the single light source 1. A thin film sample 3 corresponding to the anisotropic thin film is mounted on the sample stage 4. As described later, a reflected light from the sample 3 is detected by the CCD camera 6 and a photo-intensity distribution is displayed on the monitor 8. The beam expander 9 is used for expanding the diameter of the incident light and composed with the combination of a plurality of lenses. The condenser 10 is used for adjusting the diameter of the incident light on the light-intercepting surface of a photo detector (CCD camera).

The light projected from the single light source 1 passes through the beam expander 9, the polarizer 2, the phase converter 7, the sample 3, the analyzer 5, the condenser lenses 10, and the CCD camera 6. It is to be noted that the condenser lenses at the reflected light side may become unnecessary according to relation between the diameter of the incident light, dimension of the light-intercepting surface of the photo detector, and dimension of the area to be observed.

Figure 2:
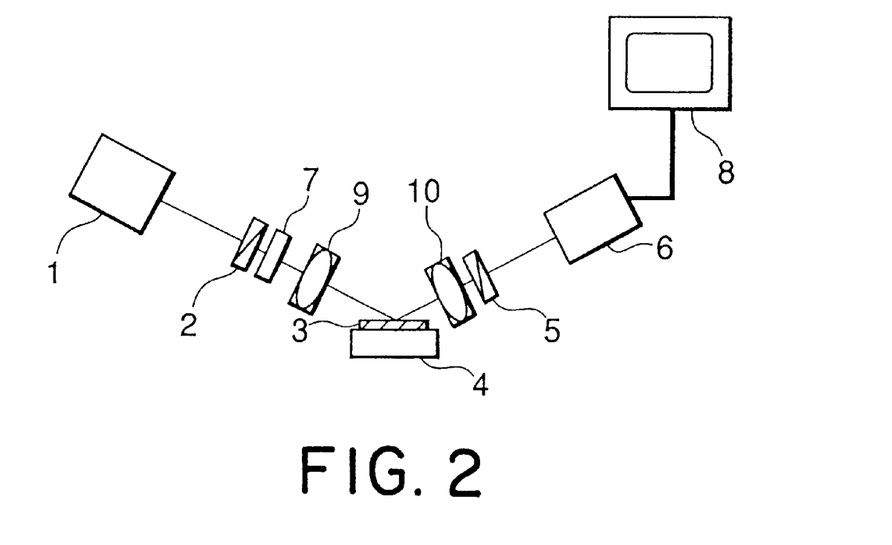
FIG. 2 is a schematic diagram of an evaluating apparatus according to a second embodiment of the present invention.

As shown in FIG. 2, the beam expander 9 arranged at the incident light side may be disposed in the down stream of the polarizer 2 and the phase converter 7. Furthermore, the condenser lenses 10 arranged on a reflected side may be disposed in the upper stream of the analyzer 5. The structure described in FIG. 2 is used when the diameter of the incident light should be increased more than an effective diameter of the optical element of such as the polarizer 2 and the phase converter 7. As the polarized state of the light is changed by passing through the lenses, the lenses of small numerical aperture which is small in change of the polarization are used for the beam splitter and the condenser, or it is desired to use the mechanism of the polarization compensation such as rectifier in the structure shown in FIG. 2.

In addition, it is capable of using a monochromatic light as the incident light obtained by a white light source and a filter, and a monochromatic light obtained by the white light source and the splitter.

Figure 3:
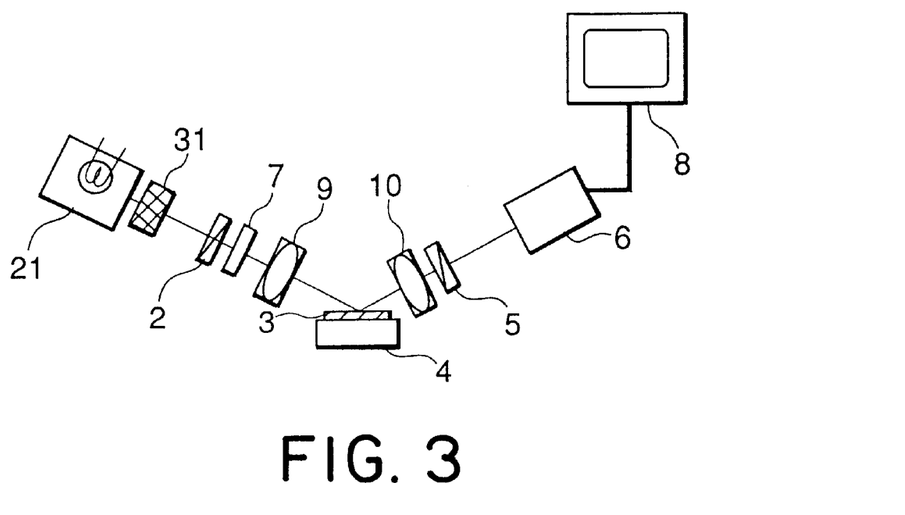
FIG. 3 is a schematic diagram of an evaluating apparatus according to a third embodiment of the present invention.
Figure 4:
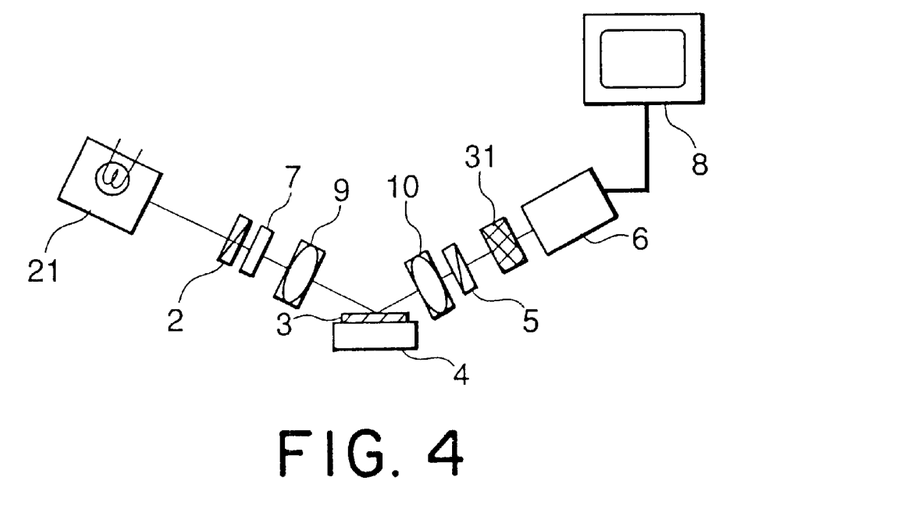
FIG. 4 is a schematic diagram of an evaluating apparatus according to a fourth embodiment of the present invention.

FIG. 3 shows an example of arrangement with the white light source. In FIG. 3, similar parts are designated by like reference numerals used in FIG. 2. A halogen lamp is used as the white light source 21. The filter 31 such as an interference filter is arranged in front of the white light source (at the incident side). As illustrated in FIG. 4, it is possible to dispose the filter 31 and the splitter (no illustrated in figure) at the reflective side.

Figure 5:
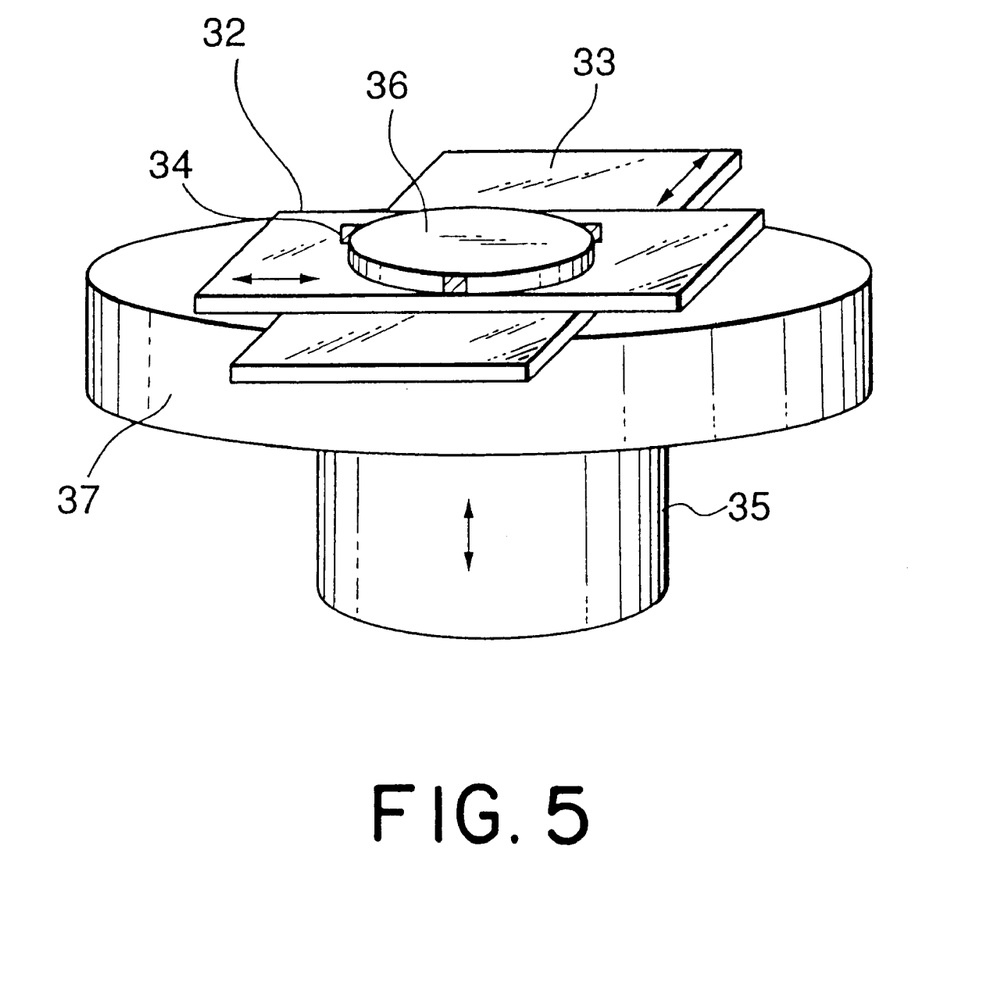
FIG. 5 is a perspective view of a sample stage used in each of the evaluating apparatuses of FIGS. 1 to 5.

Referring to FIG. 5, description will be made about a structure of the sample stage 4.

The illustrated sample stage 4 comprises a rotating mechanism and a parallel moving mechanism in the manner which will be described below. In particular, the sample stage 4 comprises a rotating stage 37, a parallel moving stage 32 and 33, the sample support 36, and an inclined angle adjusting mechanism 35, and the parallel moving stage 32 and 33 are perpendicular each other in moving direction thereof. The inclined angle of the sample support 36 is adjusted by the inclined angle adjusting mechanism 34. A height of the sample support 36 is adjusted by the parallel moving mechanism 35.

A sample was produced in accordance with the following steps and evaluated by the evaluating apparatus illustrated in FIG. 1 by using the He—Ne laser of 5 mW as the light source.

After Cr film of 500 nm in thickness is evaporated on a glass substrate (Corning 705 g), a polyimide PI-C made by Nissan Kagaku Corporation was spin-coated on the Cr film. The spin-coated glass substrate was heated at 90° C. for thirty minutes and further heated at 250° C. for sixty minutes. A measured film thickness of the polyimide film was 72 nm under the condition of the incident angle being 70° by using an ellipsometric meter MARY-102 made by Five Labo Corporation.

Next, the sample 3 was produced by rubbing with an emery roller of which diameter is 50 nm by rubbing of 0.05 of a length of penetration, 800 rpm of a rotating speed, and 30 mm/s of a substrate moving speed. When the rubbing is carried out, an area that is not subjected to the rubbing treatment was retained by covering a part of the film surface with an aluminium foil.

The sample 3 was disposed on the sample stage 4 illustrated in FIG. 5, there was projected at 50° of the incident angle the He—Ne laser beams of 3 mW in output of which the polarization direction is p polarized component and the photo detection direction is s polarized component. The diameter of the incident light was expanded till about 7 mm by the beam expander 9. A sample position was adjusted so that the incident light is provided with the area which is not subjected to the rubbing treatment.

After that, a direction of the phase converter 7 was determined as of 45°. In addition, the direction of the polarizer 2 and the analyzer 5 was adjusted so that a sum of the intensity of the light detected by the detector 6 (CCD camera) becomes minimum. In order to observe difference between the detected photo-intensities with and without the optical anisotropy, the position of the sample was moved so as to provide the light with the areas which are subjected to the rubbing treatment and are not subjected to the same. The direction of the sample was adjusted by the rotating stage 37. A rotating center of the rotating stage 37 was adjusted so as to coincide with the center of the incident light which is projected to the sample surface.

Figure 6:
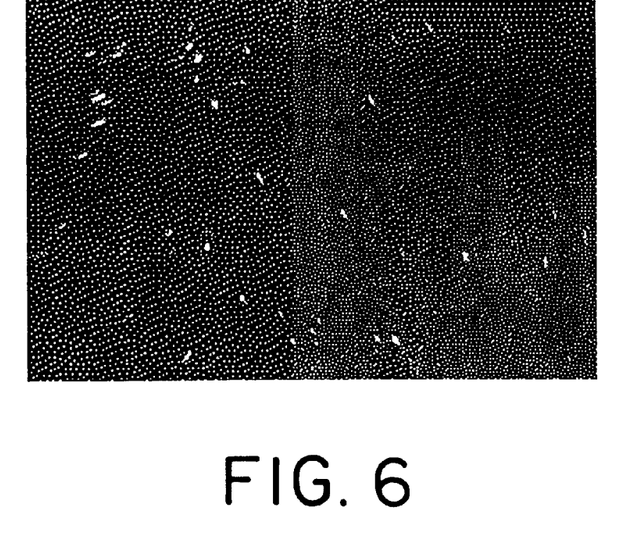
FIG. 6 shows detected intensity distribution at 0° of the sample direction in the evaluating apparatus of FIG. 1.
Figure 7:
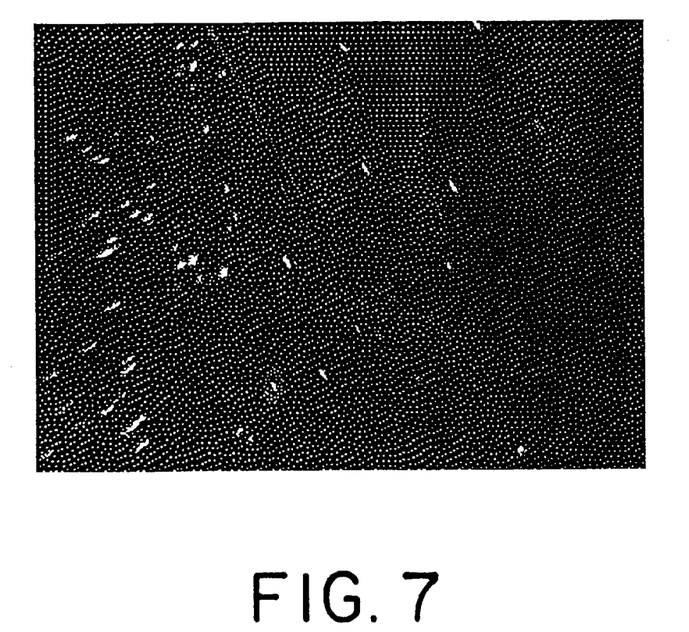
FIG. 7 shows detected intensity distribution at 45° of the sample direction in the evaluating apparatus of FIG. 1.
Figure 8:
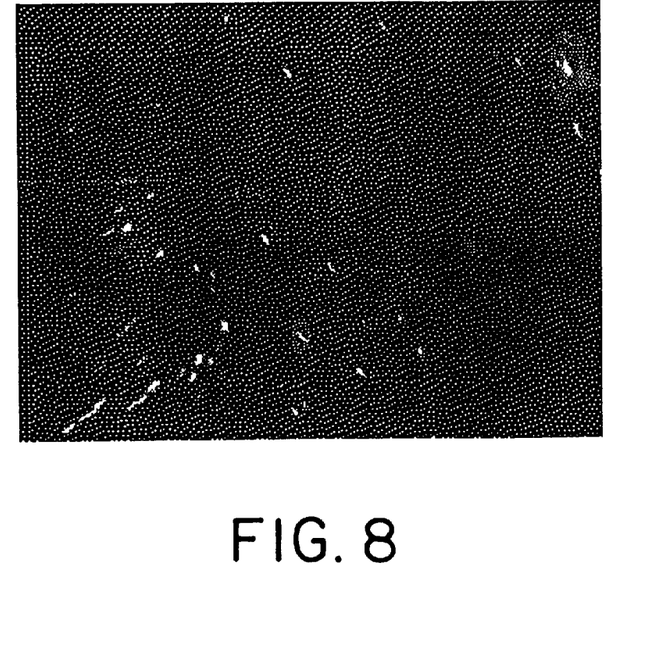
FIG. 8 shows detected intensity distribution at 90° of the sample direction in the evaluating apparatus of FIG. 1.
Figure 9:
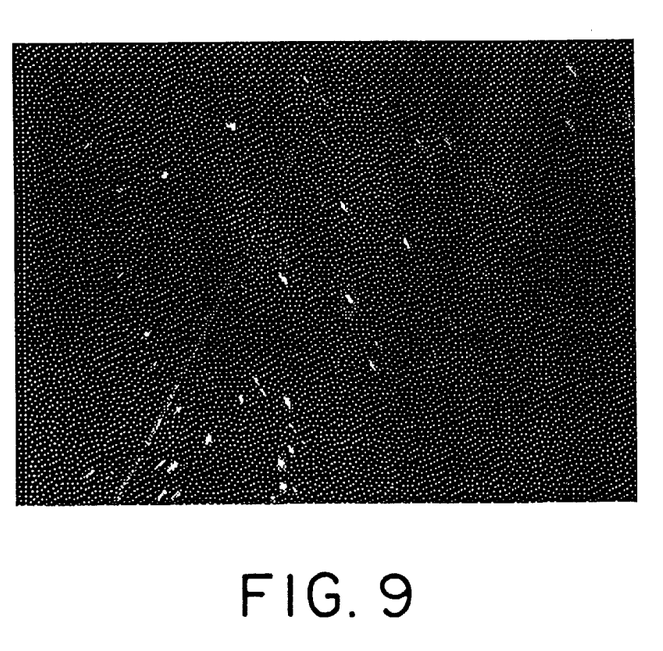
FIG. 9 shows detected intensity distribution at 135° of the sample direction of the evaluating apparatus of FIG. 1.
Figure 10:
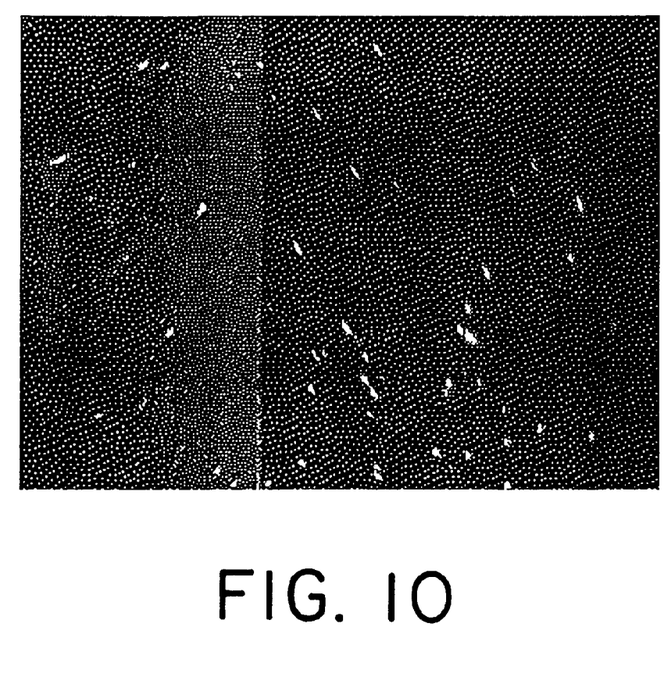
FIG. 10 shows detected intensity distribution at 180° of the sample direction of the evaluating apparatus of FIG. 1.

When the sample direction of projecting the light in perpendicular to the direction in which the rubbing treatment is made is defined as 0°, the detected intensity distribution which is obtained in each case of 0°, 45°, 90°, 135° and 180° of the sample direction is shown in FIGS. 6 to 10. In these figures, the light is projected from a left side of the figure. In FIGS. 6 to 10, the high level of detected intensity is illustrated in white. In any incident directions, the detected intensity of the area to which the rubbing treatment is subjected becomes higher than that is not subjected to the rubbing treatment. Furthermore, there is a striped pattern according to the rubbing direction on the rubbing treated area. This is because of the distribution of the optical anisotropy generated in the film. In FIG. 6, a dark area at the left side shows the area which is not subjected to the rubbing treatment, and as apparent from FIGS. 6 to 10, this shows the optical anisotropy of the rubbing treated area. Many luminescent spots found in every direction are extraneous materials inserted into the film or between the film and the substrate. As shown in these Figures, there was observed the different detected intensity at the anisotropic area in accordance with the direction of the light projected to the sample and the angle of the rubbing direction because of the anisotropy of the film.

Figure 11:
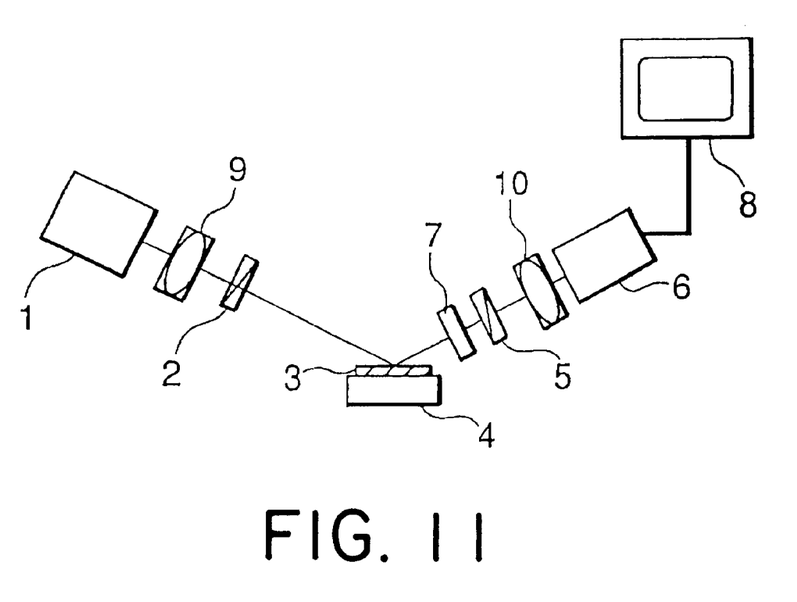
FIG. 11 is a schematic diagram of an evaluating apparatus according to a fifth embodiment of the present invention.

Although the phase converter 7 is disposed at the incident side in FIGS. 1 to 4, it may be arranged, as shown in FIG. 11, that only the polarizer 2 disposed at the incident side and that the phase converter 7 and that the analyzer 5 are disposed at the opposite side. In FIG. 11, similar parts are designated by like reference numerals in FIG. 1.

Figure 12:
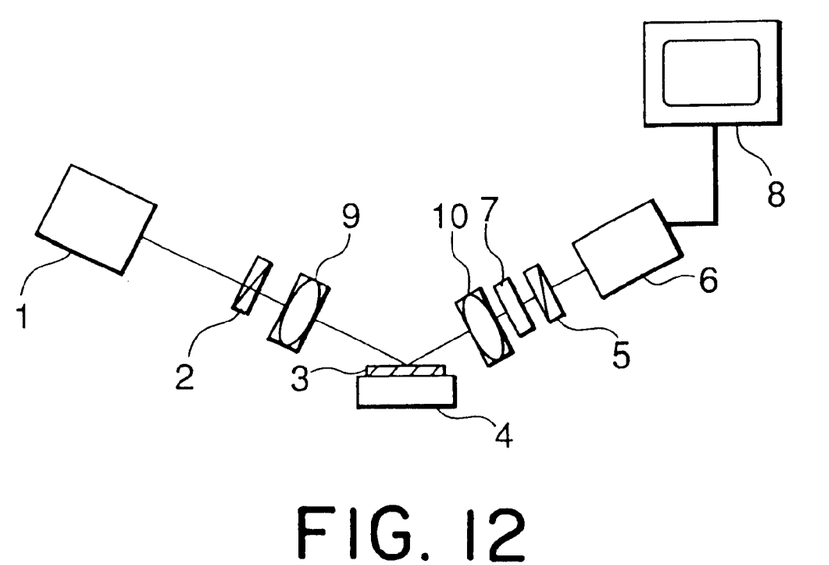
FIG. 12 is a schematic diagram of an evaluating apparatus according to a sixth embodiment of the present invention.

As shown in FIG. 12, the beam expander 9 may be arranged in the down stream of the polarizer 2 and the phase converter 7. Furthermore, the condenser lenses 10 may be arranged in the upper stream of the analyzer 5. In such a case, as the polarized state of the light is changed by passing through the lenses, it is desired to use the lenses of small numerical aperture which is small in change of the polarization for the beam splitter and the condenser, or to use the mechanism of the polarization compensation such as rectifier in the structure.

It may be possible to obtain the monochromatic light by a white light source and a filter instead of the white light source 1, and a monochromatic light can be obtained by the white light source and the splitter.

Figure 13:
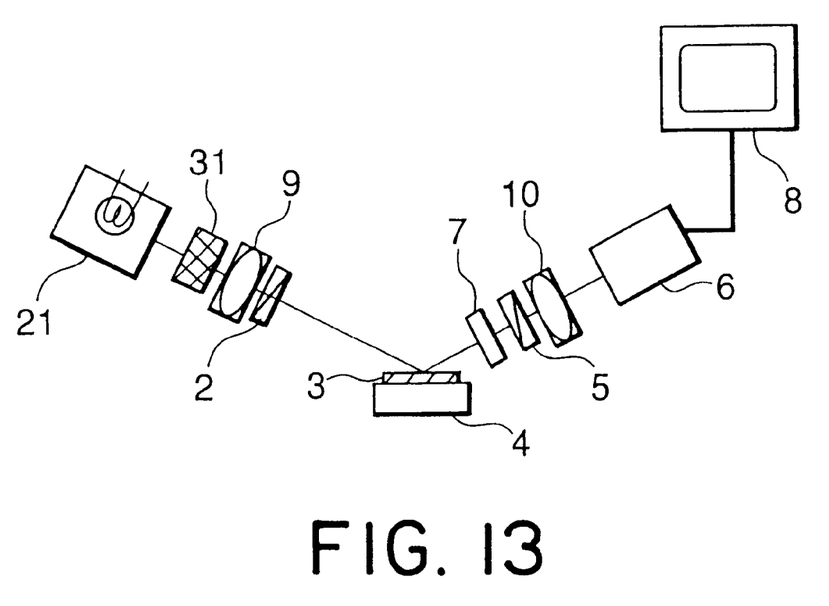
FIG. 13 is a schematic diagram of an evaluating apparatus according to a seventh embodiment of the present invention.

FIG. 13 shows an arrangement using the white light source. In FIG. 13, similar parts are designated by like reference numerals in FIG. 11. A halogen lamp is used as the white light source 21. A filter 31 such as an interference filter is arranged in front of the white light source (at the incident side).

Figure 14:
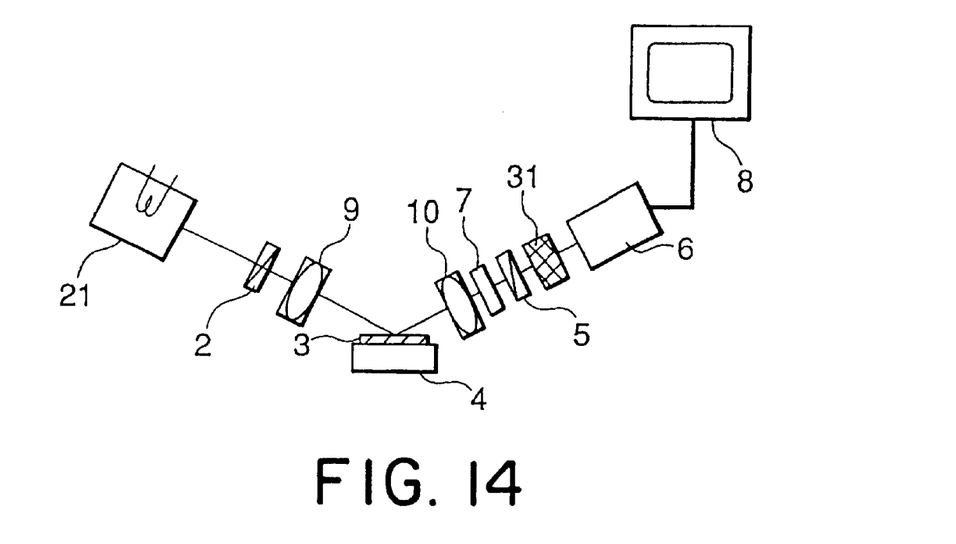
FIG. 14 is a schematic diagram of an evaluating apparatus according to an eighth embodiment of the present invention.

As illustrated in FIG. 14, it may be arranged that the filter 31 and the splitter (no illustrated in figure) are disposed at the reflective side. In FIG. 14, similar parts are designated by like reference numerals in FIG. 12.

In FIG. 13, the monochromatic light is used as the incident light by combining the 150 W of the halogen lamp, 540 nm of central wavelength, and the interference filter of 10 nm of wavelength width. As described referring to FIG. 1, the direction of the phase converter is fixed. It is possible to obtain extinction by adjusting the directions of the polarizer 2 and the analyzer 5. It is also possible to obtain the extinction by fixing the direction of the polarizer and adjusting the directions of phase converter 7 and the analyzer 5 at the opposite side. In these cases, the direction of the polarizer is defined as 45° and the linear polarization in which the s polarization component and the p polarization component is equivalent each other is used as the incident light. Incident angle is defined as 50°, and the incident light is defined as in circle having a 8 mm of the diameter.

The measured sample in this apparatus was made in accordance with the following steps. A polyimide PI-B made by Nissan Kagaku Corporation was spin-coated on the silicone substrate. A spin-coated silicone substrate was heated at 90° C. for thirty minutes, and furthermore, heated at 250° C. for sixty minutes so as to make a sample B. A measured film thickness of the polyimide film was 72 nm under the condition of the incident angle being 70° by using an ellipsometric meter MARY-102 made by Five Labo Corporation.

Next, the sample 3 was produced by rubbing twice with an emery roller of which diameter is 50 nm by rubbing of 0.05 of a length of penetration, 800 rpm of a rotating speed, and 30 mm/s of a substrate moving speed. After a part of the sample was soaked in acetone in room temperature for sixty minutes, it was dried in the air after soaking demineralized water in the room temperature.

The sample position was adjusted so as to project the incident light on the acetone treated area on the sample surface. After that, the direction of the polarizer 2 and the analyzer 5 was adjusted so that a sum of the intensity of the light detected by the detector 6 (CCD camera) becomes minimum. In order to observe difference between the detected photo-intensities with and without the optical anisotropy, the position of the sample was moved by the parallel moving stage 32 and 33 so as to provide the light with the areas which are subjected to the rubbing treatment and are not subjected to the same. The sample direction was adjusted by using the rotating stage 37. A rotating center of the rotating stage 37 was adjusted so as to coincide with the center of the incident light which is projected to the sample surface.

Figure 15:
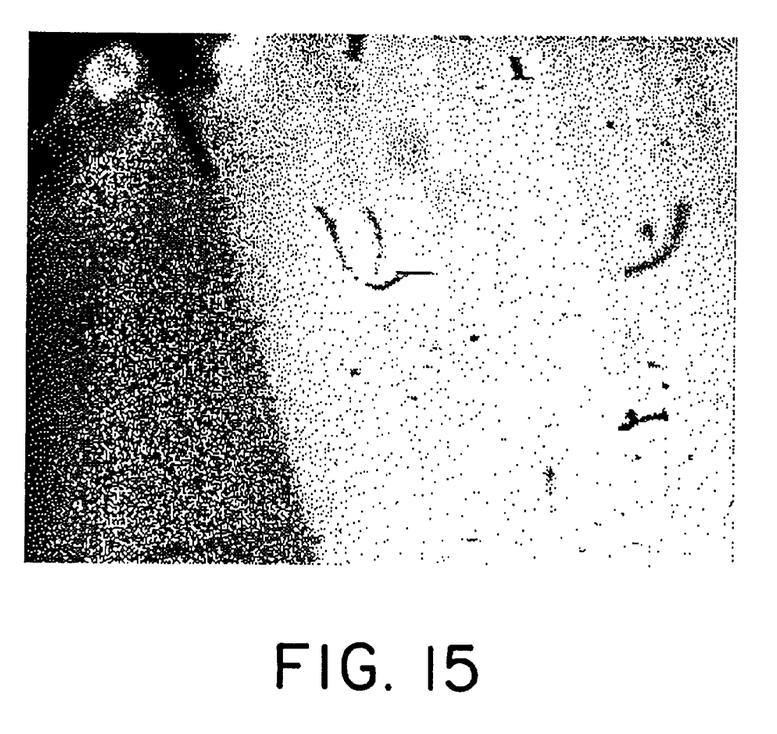
FIG. 15 shows detected intensity distribution of the sample direction of the evaluating apparatus of FIG. 13.

FIG. 15 shows the detected intensity distribution obtained by projecting the light from the direction at an angle of 60° against the rubbing direction. In FIG. 15, the light is projected to the sample from the left side of the figure, a dark area at the left side showing the area subjected to the acetone treatment. As apparent from figure, there is observed the detected intensity at the area which is not subjected to the acetone treatment is higher than that subjected to the acetone treatment. Therefore, it is found that the particle-oriented state in the film has been changed by the acetone treatment.

As mentioned above, it is possible to measure the inplane distribution of the optical anisotropy of the sample in the structure in which the white light is the light source and the phase converter is arranged at the reflected light side.

Figure 16:
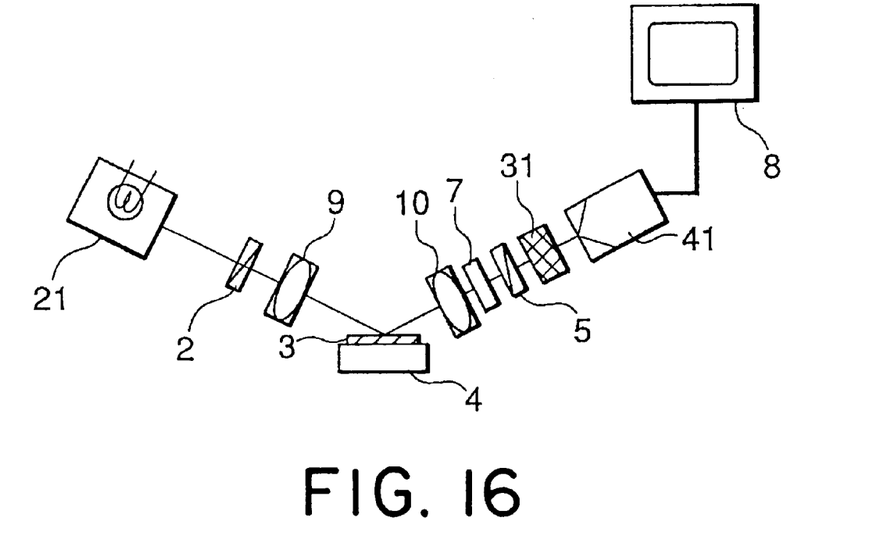
FIG. 16 is a schematic diagram of an evaluating apparatus according to a ninth embodiment of the present invention.

Referring to FIG. 16, there is illustrated an apparatus having a function of displaying the detected intensity distribution in each wavelength as a color image by combining a plurality of the transparent interference filter and a two-dimensional photo-intensity detector projecting a plurality of wavelengths, detecting the light intensity of the plurality of wavelengths of such as three-board type color CCD camera, and composing into the color image. Similar parts are designated by like reference numerals of FIG. 14.

In FIG. 16, the three-board type color CCD camera 41 is used as a two-dimensional position sensitive detector. A plurality of wavelengths are transparent by the filter 31. The intensity distribution detected by the CCD camera 41 is displayed on the monitor 8. The beam splitter may be disposed at the upper stream of the polarizer. The condenser lenses may be disposed just before the photo detector. A multi wavelength filter can be arranged at the arbitrary position between the light source and the photo detector.

In order to measure the inplane distribution of the optical anisotropy of the sample thin film, use was made of a sample similar to that described referring to the FIG. 13. The sample stage shown in FIG. 5 was used. The light source was 150 W of the halogen lamp. The incident angle was 55°. The interference filter was used which is having a peak of width of 20 nm at the transparent wavelength bands 640 nm, 530 nm, an 400 nm. The incident light was defined as the light from the beam expander having a sectional of the diameter of about 8 mm in circle. As the photo detector, the three-board type color CCD Camera (Tokyo Denshi Kougyou, good name: 3-CCD color camera CS5850) was used.

The sample position was adjusted so as to project the incident light on the acetone treated area on the sample surface. The direction of the polarizer and the analyzer were adjusted so that a sum of the intensity of the light detected by the detector (CCD camera) becomes minimum. In order to observe difference between the detected photo-intensities with and without the optical anisotropy, the position of the sample was moved so as to provide the light by the parallel moving stages 32 and 33 with the areas which are subjected to the rubbing treatment and are not subjected to the same. The sample direction was adjusted by the rotating stage 37. The rotating center of thee rotating stage 37 was adjusted so as to coincide with the center of the incident light which is projected to the sample surface.

Figure 17:
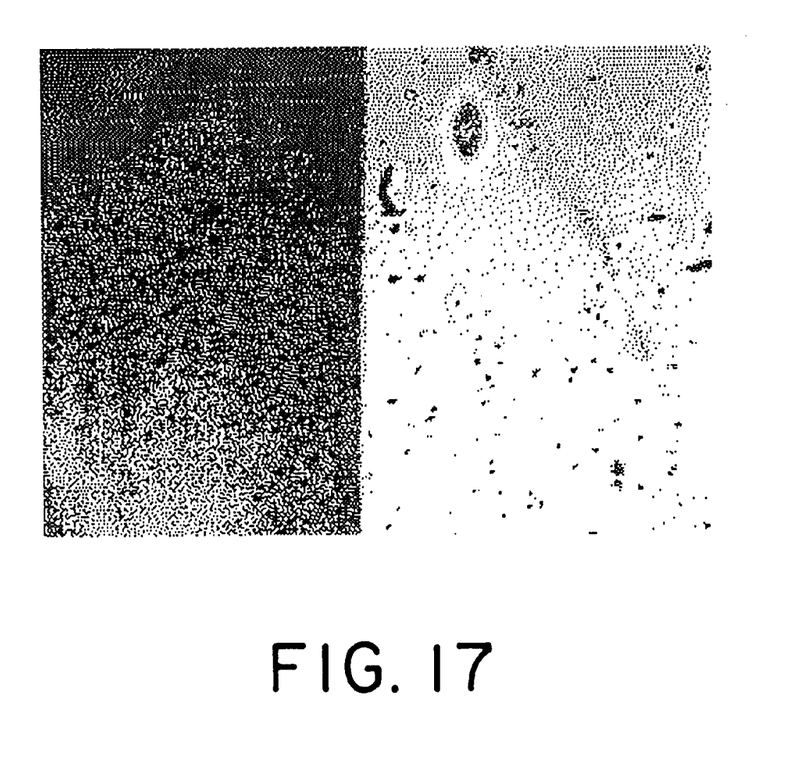
FIG. 17 shows detected intensity distribution in the evaluating apparatus of FIG. 16.

FIG. 17 shows an image obtained by measuring in condition that the 530 nm of the light is extinguished (all detected intensity in green is minimum). The light is projected from the left side of the FIG. 17, the rubbing being made from the bottom to the top. Namely, the light is projected in the direction perpendicular to the rubbing direction.

In FIG. 17, a red area at the right side is an acetone treated area, a blue area at the left side being not an acetone treated area. As illustrated in FIG. 17, it is possible to measure and display the difference a of the optical anisotropy in visual by the colors.

As mentioned above, the reflected light generated by projecting the light in the constant polarized state having a predetermined diameter by the lens system and the polarizer is passed through the phase converter and the analyzer. Received with the passed light, the two-dimensional position sensitive detector measures the detected photo-intensity distribution. Therefore, it is possible to measure the distribution of the optical anisotropy of the thin film sample in a high speed. The light may be projected by using the phase converter in addition to the lens system and the polarizer. It is preferable that use is made of the sample stage having the rotating function and the parallel moving function. Additionally, use may be of a combination of the white light source, the multi wavelength filter, and the color CCD camera.

What is claimed is:

1. A method for evaluating an anisotropic thin film, comprising the steps of:
    using a lens, a polarizer, and a phase converter to generate a light beam having a predetermined diameter and polarization state and to project said light beam as incident light into a thin film sample corresponding to said anisotropic thin film;
    detecting, by a two-dimensional photo-intensity detector through an analyzer, reflected light obtained from said thin film sample to produce a light intensity distribution; and
    evaluating an inplane distribution of an optical anisotropy of said thin film sample on the basis of said light intensity distribution.

2. A method as claimed in claim 1, further comprising a step of rotating said thin film sample on a sample inplane thereof.

3. A method as claimed in claim 1 further comprising a step of moving in parallel said thin film sample on a sample inplane thereof.

4. A method as claimed in claim 1, wherein said two-dimensional photo-intensity detector detects said reflected light through said phase converter in addition to said analyzer.

5. A method as claimed in claim 1, wherein said light beam is a laser beam.

6. A method as claimed in claim 1, wherein said light beam is white light.

7. A method as claimed in claim 6, further comprising a step of taking a specified wavelength beam from said white light to use said specified wavelength beam as said incident light.

8. A method as claimed in claim 6, further comprising a step of taking a specified wavelength beam from said reflected light to supply said specified wavelength beam to said two-dimensional photo-intensity detector.

9. A method as claimed in claim 6, wherein said two-dimensional photo-intensity detector detects intensity of a plurality of light beams different in wavelength from one another to produce a color image signal, said method comprising the steps of:
    taking said light beams from said white light, said light beams being different in wavelength from one another;
    making said two-dimensional photo-intensity detector produce a color image signal on the basis of said light beams; and
    displaying a color image on the basis of said color image signal.

10. A method as claimed in claim 6, further comprising the steps of:
    taking a plurality of light beams from said white light, said light beams being different in wavelength from one another; and
    adjusting directions of said polarizer, said phase converter, and said analyzer so that a sum of intensity of specified wavelength ones of said light beams becomes minimum.

11. An apparatus for evaluating an anisotropic thin film, comprising:
    an optical system comprising lens, a polarizer, and a phase converter, said optical system generating a light beam having a predetermined diameter and polarization state to project said light beam as incident light into a thin film sample corresponding to said anisotropic thin film;
    an analyzer disposed at an optically down stream side of said thin film sample;

a two-dimensional photo-intensity detector disposed at an optically down stream side of said analyzer for detecting reflected light, obtained from said thin film sample, through said analyzer to produce a light intensity distribution; and an evaluating unit connected to said two-dimensional photo-intensity detector for evaluating an inplane distribution of an optical anisotropy of said thin film sample on the basis of said light intensity distribution.

12. An apparatus as claimed in claim 11, further comprising a sampling stage for rotating said thin film sample on a sample inplane.

13. An apparatus as claimed in claim 11, further comprising a sampling stage for moving said thin film sample in parallel to said sample inplane.

14. An apparatus as claimed in claim 11, further comprising a phase converter disposed between said photo detector and said two-dimensional photo-intensity detector.

15. An apparatus as claimed in claim 11, wherein said light beam is a laser beam.

16. An apparatus as claimed in claim 11, wherein said light beam is white light.

17. An apparatus as claimed in claim 16, wherein said optical system comprises a wavelength selecting portion for taking a specified wavelength beam from said white light to use said specified wavelength beam as said incident light.

18. An apparatus as claimed in claim 16, further comprising a wavelength selecting portion for taking a specified wavelength beam from said reflected light to supply said specified wavelength beam to said two-dimensional photo-intensity detector.

19. An apparatus as claimed in claim 16, wherein said two-dimensional photo-intensity detector detects intensity of a plurality of light beams different in wavelength from one another to produce a color image signal, said apparatus comprising:

a wavelength selecting portion for taking said light beams from said white light, said beams being different in wavelength from one another;

an image signal producing portion for making said two-dimensional photo-intensity detector produce a color image signal; and a displaying portion connected to said image signal generating means for displaying a color image on the basis of said color image signal.

20. An apparatus as claimed in claim 16, comprising:

a wavelength selecting portion for taking a plurality of light beams from said white light, said light beams being different in wavelength from one another; and an adjusting portion for adjusting directions of said polarizer, said phase converter, and said analyzer so that a sum of intensity of specified wavelength ones of said light beams becomes minimum.

* * * * *